(12) United States Patent
Van Der Louw et al.

(10) Patent No.: US 7,169,769 B2
(45) Date of Patent: Jan. 30, 2007

(54) 17α-HYDROXY-14β-STEROIDS WITH HORMONAL EFFECT

(75) Inventors: J Jaap Van Der Louw, N.V. Organon (NL); D Dirk Leysen, N.V. Organon (NL); M.E. Marcel Evert De Gooijer, N.V. Organon (NL)

(73) Assignee: Akzo Nobel N.V., Arnhem (NL)

( * ) Notice: Subject to any disclaimer, the term of this patent is extended or adjusted under 35 U.S.C. 154(b) by 497 days.

(21) Appl. No.: 10/489,456

(22) PCT Filed: Sep. 6, 2002

(86) PCT No.: PCT/EP02/10041

§ 371 (c)(1),
(2), (4) Date: Mar. 11, 2004

(87) PCT Pub. No.: WO03/022864

PCT Pub. Date: Mar. 20, 2003

(65) Prior Publication Data
US 2004/0259849 A1    Dec. 23, 2004

(30) Foreign Application Priority Data
Sep. 12, 2001   (EP) .................................. 01203455

(51) Int. Cl.
A61K 31/58   (2006.01)
C07J 1/00    (2006.01)
(52) U.S. Cl. ....................... 514/178; 514/182; 552/647
(58) Field of Classification Search ................ 514/178, 514/182; 552/520, 647
See application file for complete search history.

(56) References Cited

U.S. PATENT DOCUMENTS

| 3,338,925 | A  | * | 8/1967 | Fried ........................... 552/646 |
| 6,391,868 | B1 | * | 5/2002 | Arnold ........................ 514/177 |
| 6,905,714 | B1 | * | 6/2005 | Ong et al. ................... 424/769 |

FOREIGN PATENT DOCUMENTS

| WO | 00/53619   | 9/2000 |
| WO | 03/022864  | 3/2003 |

OTHER PUBLICATIONS

Goodman and Gilman, 7th Edition, chapter 62, 1985.*
Csaky, "Cutting's handbook of pharmacology", pp. 390-397, 1979.*
Avery, Mitchell A. et al., Synthesis and testing of 17aβ-hydroxy-7α-methyl-D-homoestra-4,16-diene-3-one: a highly potent orally active androgen., Steroids, vol. 55, No. 2, Feb. 1990, pp. 59-64.
Toth, Istvan, et al., In Vitro Binding of 16-Methylated $C_{18}$ and $C_{19}$ Steroid Derivatives to Androgen Receptor, Pharmacological Research, vol. 32, No. 4, 1995, pp. 217-221.
Sudo, K. et al., Anti-Androgen TSAA-291. VI. Effect of the anti-androgen TSAA-291 and its related compounds on the in vitro formation of 5α-DHT-recptor complex in the cytosol of rat ventral prostate, Acta Endocrinol. (Copenhagen), Suppl. (1979), 92(229), 82-99.
Goto, Giichi et al., A stereoselective synthesis and nuclear magnetic resonance spectral study of four epimeric 17-hydroxy-16-ethylestranes, Chem Pharm. Bull. (1977), 25(6), 1295-301.
Chemical Abstract: 1995:206150, Faredin, I. et al, In vitro inhibitory effects of 16-methyl-substituted steroids on 5.alpha.-reductase in rat and human prostate, Acta Pharm. Hung. (1994), 64(5), 171-4.
Faredin, I. et al., In vitro inhibitory effects of 16-methyl-substitued steroids on 5α-reductase in rat and human prostates, Steroids, 1994, vol. 59, No. 10, pp. 568-571.
Salman, M. et al., A potential radioiodinated ligand for androgen receptor: 7a-methyl-17a-(2'=(E)-iodovinyl_19- nortestosterone, J. Med. Chem., 1991, 34, 1019-1024.
von H. Heusser, et al., Uber Steroide und Sexualhormone, Helvetica Chimica Acta, vol. 32, No. 6, 1949, pp. 2145-2151.

* cited by examiner

Primary Examiner—Barbara P. Badio
(74) Attorney, Agent, or Firm—Mark W. Milstead; William P. Ramsey, III

(57) ABSTRACT

This invention relates to steroidal compounds having the formula I

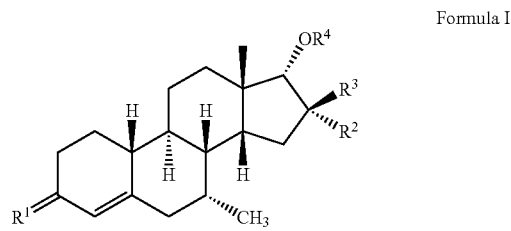

Formula I wherein: $R^1$ is O, (H,H), (H,OH), NOH, whereby OH is optionally etherified or esterified; $R^2$ and $R^3$ are independently hydrogen or ($C_{1-4}$) alkyl and at least one of $R^2$ and $R^3$ is ($C_{1-4}$) alkyl; $R^4$ is hydrogen, or ($C_{1-15}$) acyl for use in androgen-related treatments, such as androgen insufficiency and male or female contraception.

6 Claims, No Drawings

17α-HYDROXY-14β-STEROIDS WITH HORMONAL EFFECT

This application is a 371 of PCT/EP02/10041 filed Sep. 6, 2002.

The invention relates to novel 17α-hydroxy-14β-steroidal compounds and to their use in androgen-related treatments.

Steroidal compounds for use in androgen-related treatments are known, for example from the disclosures U.S. Pat. No. 3,338,925 and Jacquesy et al Bull Soc Chim France Vol 5; 1975: pp 2281–2288. In these publications 19-nor-androstane derivatives are disclosed with a 17α-hydroxy-14β stereoconfiguration. Such compounds can be used for hormonal effects, some of them more specifically for androgenic effects. The latter effects are aimed for in treatments intended to redress testosterone insufficiencies or to obtain sterility in men for contraceptive purposes. Important is that such compounds can be used for oral administration and that the duration of action is sufficiently long to reduce the need for large amounts of active compound in unit dosage forms.

This invention makes such steroids available having the formula I

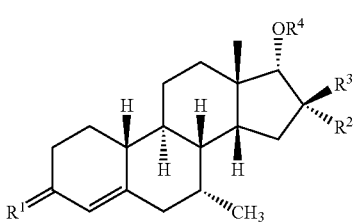

Formula I wherein:
$R^1$ is O, (H,H), (H,OH), NOH, whereby OH is optionally etherified or esterified;
$R^2$ and $R^3$ are independently hydrogen or $(C_{1-4})$ alkyl and at least one of $R^2$ and $R^3$ is $(C_{1-4})$ alkyl;
$R^4$ is hydrogen, or $(C_{1-15})$ acyl.

It is found that these compounds are not only having high androgenic potency, but also are highly resistent to liver metabolism. Low exposure to active compound is important to reduce the risk for adverse effects. The utility is unexpected, also in view of the publication Heusser et al Helv Chim Acta Vol 22, 1949 pp 1245–1251, in which it is reported that 17α-hydroxy-14β-testosterone has no androgenic activity.

A particular favourable profile for use in oral medicines for androgen-related treatments is displayed by a compound having formula I wherein $R^1$ is oxo and at least one of $R^2$ and $R^3$ is methyl and the other is hydrogen or methyl. A specifically preferred compound of the invention is (7α,14β,16β,17α)-17-hydroxy-7,16-dimethylestr-4-en-3-one.

The term $(C_{1-4})$ alkyl as used in the definition of formula I means a branched or unbranched alkyl group having 1–4 carbon atoms, like methyl, ethyl, propyl, isopropyl, butyl, isobutyl, and tertiary butyl. Preferred alkyl groups are methyl and ethyl.

The term $(C_{1-15})$ acyl means an acyl group derived from a carboxylic acid having 1–15 carbon atoms, like formyl, acetyl, propanoyl, butyryl, 2-methylpropanoyl, pentanoyl, pivaloyl, hexanoyl etc. Also included within the definition of $(C_{1-15})$ acyl are acyl groups derived from dicarboxylic acids, like hemi-maloyl, hemi-succinoyl, hemi-glutaroyl, and so on. Preferred is hemi-succinoyl.

The invention also pertains to the compounds described hereinbefore as a medicine. The compounds can be used in, i.a. male contraception and male or female hormone replacement therapy. In general the aim of such a treatment is to obtain an androgenic effect in an organism, such as an animal or a human person. Therefore such a treatment is referred to in this description as an androgen-related treatment. Thus the invention also pertains to a method of treatment of an animal or a human person in need of androgenic stimulation for an androgenic effect by administering an effective amount of any of the above compounds to the animal or human person. More specifically, the invention pertains to a method of treatment of androgen insufficiency, by administering to a human male or female an effective amount of any of the above compounds. The invention also is in the use of any of the above compounds for the preparation of a medicine for treating androgen insufficiency. In the context of the invention, the term "androgen insufficiency" is to be understood to pertain to all kinds of diseases, disorders, and symptoms in which a male or a female suffers from too low a testosterone level, such as in hypogonadal men. In particular, the androgen insufficiency to be treated by the compound of the invention is the reduction of the testosterone level which a human male incurs as a result of age (the compound of the invention is then used for male hormone replacement therapy), or when he is subject to male contraception. In the context of male contraception, the compound of the invention especially serves to neutralise the effect of regimens of male hormone contraception in which a sterilitant such as a progestagen or LHRH (luteinizing hormone releasing hormone) is administered regularly, e.g. daily, or it is used as the sole male contraceptive substance.

The androgens can be administered principally via any suitable route available to the skilled person. As indicated above, oral administration is preferred, most preferably in the form of a solid dosage unit such as a tablet or a capsule. The invention also relates to pharmaceutical formulations comprising a compound as described hereinbefore and a pharmaceutically acceptable carrier. Thus the carrier may be in a solid form or liquid form, and the formulation may be an oral dosage unit such as a tablet or an oral solution, e.g. in a capsule. Methods and compositions for making such dosage units are well-known to those skilled in the art. For example, conventional techniques for making tablets and pills, containing active ingredients, are described in the standard reference, Gennaro et al, Remington's Pharmaceutical Sciences, (18th ed., Mack Publishing Company, 1990, see especially Part 8: Pharmaceutical Preparations and Their Manufacture). The compound can also be administered via an implant, a patch, or any other suitable device for the sustained release of an androgen composition.

The dose of and regimen of administration of the compounds of the invention, or a pharmaceutical composition thereof, to be administered will obviously depend on the therapeutic effect to be achieved and will vary with the route of administration, and the age and condition of the individual subject to whom the medicament is to be administered, and/or or the particular contraceptive or HRT regimen in which it is used. Typical dosage amounts are 0.001–5 mg per kg body weight.

The compounds of the invention may be produced by various methods known in the art of organic chemistry in general, and especially in the art of the chemistry of steroids (see, for example: Fried, J. et al, *Organic Reactions in Steroid Chemistry*, Volumes I and II, Van Nostrand Reinhold Company, New York, 1972).

A convenient starting material for the preparation of compounds of formula I wherein $R^1$ is oxo, $R^2$ and $R^3$ have the previously given meaning; and $R^4$ is hydrogen, is for instance a compound of general formula II, whose synthesis is described in WO 00/53619.

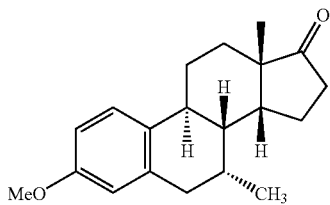

Formula II

A possible synthesis route for compounds of the invention starts with the alkylation of compounds of formula II at C-16, usually resulting in the predominant or specific formation of the 16β-isomer [for alkylation reactions, see e.g. Carey, F. A., Sundberg, R. J., "Advanced Organic Chemistry", Part B: Reactions and Synthesis, Chapter 1, Plenum Press, NY, 1990]. Optionally, the stereochemistry at C-16 can be inverted by deprotonation followed by hydrolysis. If desired, alkylation at C-16 can be followed by a second alkylation reaction at the same position, using the same or another alkylating agent, resulting in 16,16-dialkylated compounds.

The carbonyl group at C-17 is reduced using $NaBH_4$, $LiAlH_4$, or other hydride-donor reagents, which leads to the predominant or specific formation of the 17α-hydroxy compound.

Birch reduction [Caine, D., in Org. Reactions 23, p. 1, Wiley, N.Y., 1976] of the 16-substituted (14β,17α)-3-methoxyestra-1,3,5(10)-trien-17-ol and, finally, hydrolysis of the resulting 2,5(10)-diene produces a 16-substituted (14β,17α)-17-hydroxyestr-4-en-3-one derivative of the invention.

Compounds of the invention in which $R^1$ is (H,H), (H,OH), or NOH, whereby OH is optionally etherified or esterified, are obtained, by using methods known in the art, from compounds of formula I in which $R^1$ is oxo.

The invention will be further explained hereinafter with reference to the following Examples.

EXAMPLE 1

(7α,14β,16β,17α)-17-Hydroxy-7,16-dimethylestr-4-en-3-one i)—A solution of lithium bis(trimethylsilyl)amide (55.5 mmol) in tetrahydrofuran (96 ml) was cooled to −40° C. A solution of (7α,14β)-3-methoxy-7-methylestra-1,3,5(10)-trien-17-one (WO 00/53619; 15.0 g) in dry tetrahydrofuran (66 ml) was added dropwise and the reaction mixture was stirred for 45 min. Then, at −30° C., iodomethane (6.3 ml) was added and stirring was continued for 1 h (−30<T−20° C.). The mixture was poured into a saturated aqueous solution of ammonium chloride and the product was extracted into ethyl acetate. The combined organic phases were washed with water and brine, dried over sodium sulfate and concentrated under reduced pressure, to give (7α,14β,16β)-3-methoxy-7,16-dimethylestra-1,3,5(10)-trien-17-one (17.33 g). The product was used in the following step without further purification.

ii)—A solution of the product obtained in the previous step (1.0 g) in tetrahydrofuran (19 ml), methanol (9.5 ml), and water (5.6 ml), cooled to −7° C., was treated with sodium borohydride (0.35 g). After 1 h stirring at 0° C., another portion of sodium borohydride (0.35 g) was added and stirring was continued for 1 h. The reaction mixture was poured into water and the product was extracted into ethyl acetate. The combined organic phases were washed with a saturated aqueous solution of sodium hydrogencarbonate and brine, dried over sodium sulfate and concentrated under reduced pressure. Column chromatography afforded (7α,14β,16β,17α)-3-methoxy-7,16-dimethylestra-1,3,5(10)-trien-17-ol (1.06 g).

iii)—The product obtained in the previous step (0.98 g) in dry tetrahydrofuran (34 ml) was added to a solution of lithium (2.15 g) in liquid ammonia (244 ml), cooled to −50° C. The reaction mixture was stirred at a temperature between −50° C. and −40° C. for 5 h. Ethanol was added and the ammonia was allowed to evaporate. Water was added and the product was extracted into ethyl acetate. The combined organic phases were washed with water and brine, dried over sodium sulfate and concentrated under reduced pressure, to give (7α,14β,16β,17α)-3-methoxy-7,16-dimethylestra-2,5(10)-dien-17-ol (1.03 g). The product was used in the following step without further purification.

iv)—A solution of the product obtained in the previous step (1.03 g) in acetone (57 ml) was treated with concentrated hydrochloric acid (2.9 ml). After 2 h stirring at room temperature, the reaction mixture was poured into water. The product was extracted into ethyl acetate; the combined organic phases were washed with a saturated aqueous solution of sodium hydrogencarbonate and brine, dried over sodium is sulfate and concentrated under reduced pressure. Column chromatography afforded (7α,14β,16β,17α)-17-hydroxy-7,16-dimethylestr-4-en-3-one (0.54 g), $[α]_D^{20}=+98.0°$ (c=0.50, dioxane).

EXAMPLE 2

(7α,14β,16α,17α)-17-Hydroxy-7,16-dimethylestr-4-en-3-one i)—A solution of lithium bis(trimethylsilyl)amide (29 mmol) in tetrahydrofuran (45 ml) was cooled to −40° C. A solution of (7α,14β,16β)-3-methoxy-7,16-dimethylestra-1,3,5(10)-trien-17-one (Example 1, step i; 6.0 g) in dry tetrahydrofuran (24 ml) was added dropwise and the reaction mixture was stirred for 1 h. Then it was quenched by addition of a saturated aqueous solution of ammonium chloride and the product was extracted into ethyl acetate. The combined organic phases were washed with a saturated aqueous solution of ammonium chloride, water and brine, dried over sodium sulfate and concentrated under reduced pressure, to give (7α,14β,16α)-3-methoxy-7,16-dimethylestra-1,3,5(10)-trien-17-one (6.82 g). The product was used in the following step without further purification.

ii)—Following a procedure analogous to that described under ii of Example 1, the product obtained in the previous step (1.0 g) was converted to (7α,14β,16α,17α)-3-methoxy-7,16-dimethylestra-1,3,5(10)-trien-17-ol (0.62 g).

iii)—Following a procedure analogous to that described under iii of Example 1, the product obtained in the previous step (0.58 g) was converted to (7α, 14β, 16α, 17α)-3-methoxy-7,16-dimethylestra-2,5(10)-dien-17-ol (0.59 g).

iv)—Following a procedure analogous to that described under iv of Example 1, the product obtained in the previous step (0.59 g) was converted to (7α,14β,16α,17α)-17-hydroxy-7,16-dimethylestr-4-en-3-one (0.20 g), $[\alpha]_D^{20}$=+91.3° (c=0.48, dioxane).

EXAMPLE 3

(7α,14α,17α)-17-Hydroxy-7,16,16-trimethylestr-4-en-3-one i)—Following a procedure analogous to that described under i of Example 1, (7α,14β,16β)-3-methoxy-7,16-dimethylestra-1,3,5(10)-trien-17-one (Example 1, step i; 6.0 g) was converted to (7α,14β)-3-methoxy-7,16,16-trimethylestra-1,3,5(10)-trien-17-one (5.99 g).

ii)—Following a procedure analogous to that described under ii of Example 1, the product obtained in the previous step (1.0 g) was converted to (7α,14β,17α)-3-methoxy-7,16,16-trimethylestra-1,3,5(10)-trien-17-ol (0.39 g).

iii)—Following a procedure analogous to that described under iii of Example 1, the product obtained in the previous step (0.32 g) was converted to (7α,14β,17α)-3-methoxy-7,16,16-trimethylestra-2,5(10)-dien-17-ol (0.38 g).

iv)—Following a procedure analogous to that described under iv of Example 1, the product obtained in the previous step (0.38 g) was converted to (7α,14β,17α)-17-hydroxy-7,16,16-trimethylestr-4-en-3-one (0.10 g), $[\alpha]_D^{20}$=+81.1° (c=0.55, dioxane).

EXAMPLE 4

In a manner analogous to the procedures described in Examples 1 and 3, and using (7α,14β)-3-methoxy-7-methylestra-1,3,5(10)-trien-17-one (WO 00/53619) as starting material, the following products were prepared:
(a) (7α,14β,16β,17α)-16-Ethyl-17-hydroxy-7-methylestr-4-en-3-one, $[\alpha]_D^{20}$=+109° (c=1.00, dioxane).
(b) (7α,14β,16β,17α)-16-Ethyl-17-hydroxy-7,16-dimethylestr-4-en-3-one, $[\alpha]_D^{20}$=+89° (c=1.00, dioxane) [via alkylation of starting material with iodomethane followed by alkylation with iodoethane].

EXAMPLE 5

(7α,14β,17α)-17-Hydroxy-7-methylestr-4-en-3-one (reference compound 2)

i)—A solution of (7α,14β)-3-methoxy-7-methylestra-1,3,5(10)-trien-17-one (WO 00/53619; 2.8 g) in dry ethanol (100 ml), cooled to 4° C., was treated with sodium borohydride (0.70 g). After 1 h stirring, another portion of sodium borohydride (0.35 g) was added and stirring was continued for 3 h. Aqueous acetic acid (50%, 10 ml) was added dropwise and the reaction mixture was poured into water. The product was extracted into dichloromethane; the combined organic phases were washed with a saturated aqueous solution of sodium hydrogencarbonate and brine, dried over sodium sulfate and concentrated under reduced pressure, to give (7α,14β,17α)-3-methoxy-7-methylestra-1,3,5(1.0)-trien-17-ol (2.93 g). The product was used in the following step without further purification.

ii)—Following a procedure analogous to that described under iii of Example 1, the product obtained in the previous step (3.40 g) was converted to (7α,14β,17α)-3-methoxy-7-methylestra-2,5(10)-dien-17-ol (3.50 g).

iii)—Following a procedure analogous to that described under iv of Example 1, the product obtained in the previous step (3.30 g) was converted to (7α,14β,17α)-17-hydroxy-7-methylestr-4-en-3-one (1.50 g), m.p. 148.5–149.3° C., $[\alpha]_D^{20}$=+102° (c=1.00, dioxane).

EXAMPLE 6

Androgen Activity

The transactivative androgen activity of the compounds of the invention was measured in Chinese hamster ovary cells (CHO) transfected with the human androgen receptor (hAR), in combination with a mouse mammary tumor virus (MMTV), and luciferase receptor gene (incubation time 16 h, temperature 37° C.) and compared with the activity of 5α-dihydrotestosterone [Schoonen, W. G. E. J.; de Ries, R. J. H.; Joosten, J. W. H.; Mathijssen-Mommers, G. J. W.; Kloosterboer, H. J., Analyt. Biochem. 261, 222–224 (1998)]. Results are collected in Table 1.

EXAMPLE 7

Determination of $t_{1/2}$ of Androgens of the Invention After Incubation with Human Hepatocytes The half-life of a compound as a result of contact with human hepatocytes holds as a reliable indication of metabolic stability. As it is well known that the absorption of this class of steroids is high, this assay provides an in vitro model for oral activity in humans. It will be understood that a shorter half-life indicates that a compound will be metabolized more rapidly or, vice versa, the longer the half-life, the better the compound may exert its effect upon the human body when administered orally.

Hepatocytes collected from healthy young (25–45 year) male organ donors were cryo preserved in liquid nitrogen and kept there until use. They were thawed at 37° C. in a waterbath, placed immediately on ice, washed twice in one volume of cold (4° C.) incubation medium [William's medium E (without phenol red) with Glutamax I®, gentamicin 50 µg/ml, insulin 1 µM, fetal calf serum 0% (v/v)], counted and the viability checked by Trypan blue exclusion. Cells were incubated as suspensions in 96-wells (non-coated) plates at a nominal density of $3 \times 10^4$ cells/well in 300 µl medium at 37° C. with an air/CO$_2$ mixture (95/5).

The hepatocytes were incubated with 100 nM final concentration of the compound to be tested. The incubations were stopped after 0.5, 1 and 2 h by centrifugation at 200 g. The supernatant was collected for liquid chromatography coupled to immediate mass spectroscopic analysis (LC-MS/MS analysis) and for bioassay. For the latter 10 µl was used for determination of the androgenic activity. The androgenicity was determined as described at example 6. The final compound concentration for determination of androgenic activity was 1 nmol/l.

Results

The metabolic stability ($t_{1/2}$) of the compounds of the invention were classified according to the following scheme:
(+++) metabolic stability>17α-methyltestosterone (MT)
(++) 17α-methyltestosterone>metabolic stability>80% of 17α-methyltestosterone
(+) 80% of 17α-methyltestosterone>metabolic stability>testosterone
(−) metabolic stability<testosterone Results are collected in Table 1.

TABLE 1

Androgen activity and metabolic stability ($t_{1/2}$) of the compounds of the invention.

| Example | Androgen activity (%) | $t_{1/2}$ LC-MS/MS | Bioassay |
|---|---|---|---|
| 1 | 99.0 | (++) | (++) |
| 2 | 38.7 | (+) | (++) |
| 3 | 78.5 | *a) | (+) |
| 4a | 20.0 | * | (−) |
| 4b | 24.0 | * | (+) |
| Ref. comp. 1[b] | 0.5 | | (−) |
| Ref. comp. 2[c] | 60.5 | | (−) | a)* means that no data or no reliable data are available
[b](14β, 17α)-17-Hydroxyestr-4-en-3-one (U.S. Pat. No. 3,338,925).
[c](7α, 14β, 17α)-17-Hydroxy-7-methylestr-4-en-3-one (Example 5).

The invention claimed is:

1. A steroidal compound having the formula I

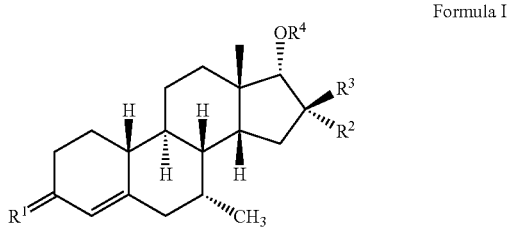

Formula I wherein:

$R^1$ is O, (H,H), (H,OH), NOH, whereby OH is optionally etherified or esterified;

$R^2$ and $R^3$ are independently hydrogen or ($C_{1-4}$) alkyl and at least one of $R^2$ and $R^3$ is ($C_{1-4}$) alkyl;

$R^4$ is hydrogen, or ($C_{1-5}$) acyl.

2. The steroidal compound according to claim 1, wherein $R^1$ is O and least one of $R^2$ and $R^3$ is methyl and the other is hydrogen or methyl.

3. The steroidal compound according to claim 2, wherein the compound is (7α,14β,16β,17α)-17-hydroxy-7,16-dimethylestr-4-en-3-one.

4. A method of male contraception or male or female hormone replacement therapy, comprising:
administering an effective amount of the compound according to claim 1.

5. A method of treatment of an animal or a human person in need of androgenic stimulation for an androgenic effect, comprising:
administering an effective dose of the steroidal compound according to claim 1 to the animal or human person.

6. A pharmaceutical composition, comprising:
the compound according to claim 1, and
pharmaceutically acceptable auxiliaries.

* * * * *